United States Patent [19]
Yoshimura et al.

[11] Patent Number: 4,808,737
[45] Date of Patent: Feb. 28, 1989

[54] PROCESS FOR PRODUCING 2-HYDROXY-4-METHYLTETRAHYDROPYRAN

[75] Inventors: Noriaki Yoshimura; Yasuo Tokitoh, both of Kurashiki, Japan

[73] Assignee: Kuraray Co., Ltd., Kurashiki, Japan

[21] Appl. No.: 921,383

[22] Filed: Oct. 22, 1986

[30] Foreign Application Priority Data

Nov. 5, 1985 [JP] Japan ................................ 60-248466

[51] Int. Cl.$^4$ ........................................... C07D 309/10
[52] U.S. Cl. .................................................. 549/423
[58] Field of Search ......................................... 549/423

[56] References Cited

FOREIGN PATENT DOCUMENTS 0155002 9/1985 European Pat. Off. .
2404312 8/1975 Fed. Rep. of Germany .

OTHER PUBLICATIONS

*Chemical Abstracts,* 103:22459d (1985).
*Chemical Abstracts,* 87:167,499c (1977).

Primary Examiner—Nicky Chan
Attorney, Agent, or Firm—Oblon, Fisher, Spivak, McClelland & Maier

[57] ABSTRACT

The hydroformylation of 3-methyl-3-buten-1-ol with hydrogen and carbon monoxide, when carried out under relatively mild conditions, gives 2-hydroxy-4-methyltetrahydropyran (MHP) in high rate of reaction and in high selectivity even in a very low rhodium catalyst concentration. MHP is useful as a starting material for the production of 3-methyl-1,5-pentanediol and $\beta$-methyl-$\delta$-valerolactone which are in turn usable as raw materials for producing polyesters and polyurethanes. The process according to the invention can give such MHP advantageously from the industrial viewpoint and has very great industrial utility.

7 Claims, No Drawings

PROCESS FOR PRODUCING 2-HYDROXY-4-METHYLTETRAHYDROPYRAN

BACKGROUND OF THE INVENTION

1. Field of the Invention

This invention relates to a process for producing 2-hydroxy-4-methyltetrahydropyran. More particularly, the invention relates to an improved process for producing 2-hydroxy-4-methyltetrahydropyran (hereinafter referred to briefly as MHP) which comprises hydroformylating 3-methyl-3-buten-1-ol under specific conditions.

2. Description of the Prior Art

The reaction of an olefin with hydrogen and carbon monoxide in the presence of a rhodium catalyst, which gives an aldehyde, is well known generally as hydroformylation.

However, it has been found that even if the hydroformylation reaction is conducted using the same catalyst under the same conditions, there is a marked difference between different olefins or olefinic compounds. By way of illustration, compared with a straight-chain olefin, a branched olefin is tens of times slower to react (Chem. Ber., 1969, 102). It is also known that functionally substituted olefinic compounds such as allyl alcohol and vinyl acetate show quite different reactivities than olefins having no functional group because the double bond and functional group in the former may coordinate to the rhodium atom in the manner of chelation [J. Molecular Cat., 18 (1983), 381 and ibid., 16 (1982), 195]. It has also been found that even when a given olefin is subjected to hydroformylation under a given set of conditions, the difference in the kind of ligand in the catalyst results in a marked difference in reactivity. If, for example, in the hydroformylation of an α-olefin such as 1-octene, in the presence of a rhodium catalyst, tris(2-phenylphenyl) phosphite or tris(2,6-dimethylphenyl) phosphite is employed as the ligand, both the reaction rate and the selectivity to the straight-chain aldehyde are remarkably lower than it is the case when triphenylphosphine or triphenyl phosphite is used. [J. Org. Chem., 34 (1969), 327]. On the other hand, in the hydroformylation of a branched olefin such as 2-methyl-1-hexene in the presence of a rhodium catalyst, the use of tris(2,6-dimethylphenyl) phosphite as the ligand tends to give similar results and rather, in this case of 1-octene, the reactivity is further depressed and virtually no reaction takes place. However, it is known that when tris(2-phenylphenyl) phosphite is used as the ligand, the result is the reverse of that found for 1-octene, i.e. a higher reactivity is obtained than it is the case when triphenylphosphine is employed (Japanese Patent Application Laid-Open No. 123134/1982). Thus, it is known that the hydroformylation differs markedly in reactivity according to the kind of olefin or olefinic compound and the kind of ligand. When a hydroformylation reaction is conducted advantageously on a commercial scale in the presence of a rhodium catalyst, it is difficult to predetermine the optimum combination of olefin or olefinic compound with ligand.

In regard to the hydroformylation of 3-methyl-3-buten-1-ol (hereinafter referred to briefly as IPEA) which is an exemplary olefinic compound and is used in the practice of the present invention, all that is known is that the hydroformylation is carried out using a rhodium catalyst having as the ligand an organic tertiary phosphine, typically triphenyl phosphine (Japanese Patent Application Laid-Open No. 106910/1975).

The above laid open patent application No. 106910/1975 so states that in order to assure a satisfactory reaction rate in the hydroformylation reaction of IPEA using triphenylphosphine as the ligand, the rhodium catalyst should be used in a high concentration and, moreover, in this literature the hydroformylation is conducted at a high reaction pressure of 250 atms.

The hydroformylation of IPEA, when discussed from the industrial viewpoint, can hardly be said economical if the expensive rhodium catalyst cannot be recovered for repeated use for a long period. The higher the concentration of the rhodium catalyst is, the more important this aspect becomes. Since, however, the hydroformylation product from IPEA is a compound very readily acetalizable, the rhodium catalyst is deteriorated by heat or by accumulation of high-boiling products even when attempts are made to recycle the catalyst for reuse while maintaining the catalyst activity for a prolonged period of time. Such problems in commercial production have not been solved yet. As regards the reaction pressure, the higher the reaction pressure is, the greater the number of problems is which are encountered relative to reaction apparatus. This is a matter of course but, for decreasing the reaction pressure in the above reaction system, it is necessary to use triphenylphosphine in large amounts relative to rhodium so that the rhodium catalyst can be stabilized. However, when triphenylphosphine is used in large excess relative to rhodium at low pressures, the rate of reaction falls drastically and, in extreme cases, the reaction hardly proceeds. Thus, another problem is encountered.

On the other hand, it is described in Japanese Patent Application Laid-Open No. 123134/1982 that in the case of those olefins that have no functional groups, for example 2-methyl-1-hexene, the use of tris(2-t-butylphenyl) phosphite as the ligand leads to higher reactivity as compared with the use of triphenylphosphine.

However, it was found that when IPEA, which is the starting material in the process according to the present invention and contains a double bond and a hydroxyl group which can coordinate to the rhodium atom, is subjected to hydroformylation under the conditions described in the above-cited Japanese Patent Application Laid-Open No. 123134/1982, not only was the reaction rate low but the selectivity to the desired product compound was extremely low. It was evident, therefore, that such a process cannot be practiced advantageously on a commercial scale.

SUMMARY OF THE INVENTION

It is an object of the invention to provide a process for producing MHP by hydroformylating IPEA which is practicable at relatively low pressures.

Another object of the invention is to provide a process for producing MHP by hydroformylating IPEA which is practicable in a low rhodium catalyst concentration, hence advantageous from the industrial standpoint.

A further object of the invention is to provide a process for producing MHP by hydroformylating IPEA by which MHP can be obtained at a high rate of reaction and in a high selectivity.

The above objects can be accomplished by carrying out the MHP formation reaction between IPEA and a mixed gas composed of hydrogen and carbon monoxide in the presence of a rhodium compound in a concentration of 0.01–0.1 milligram atom (as rhodium) per liter and in the simultaneous presence of a tris(substituted aryl) phosphite represented by the formula $P(OR)_3$ wherein the three Rs are the same or different and each R is a substituted aryl group and having an electronic parameter ($\nu$-value) of 2080–2090 cm$^{-1}$ and steric parameter ($\theta$-value) of 135°–190° in an amount of 110–500 moles per gram atom of rhodium.

DETAILED DESCRIPTION OF THE INVENTION

The tris(substituted aryl) phosphite to be used in accordance with the invention is required to have an electronic parameter ($\nu$-value) of 2080–2090 cm$^{-1}$ and a steric parameter of ($\theta$-value) of 135°–190°. If at least one of these parameters is outside the above-specified range, such high rate of reaction and such high selectivity toward MHP as obtainable in accordance with the invention will never be attained.

The terms "electronic parameter ($\nu$-value)" and "steric parameter ($\theta$-value)" as used herein are the values defined by C. A. Tolman [Chem. Rev.,177 (1977), 313]. Thus, the $\nu$-value is defined as the CO stretching frequency of $Ni(CO)_3L$ (L being the phosphorus ligand) in the infrared absorption spectrum measured in $CH_2Cl_2$ and the $\theta$ value is defined as the apex angle of a cone, centered 2.28 Å from the center of the phosphorus atom, which just touches the van der Waals radii of the outermost atoms of that group which is bonded to the phosphorus atom.

The tris(substituted aryl) phosphite to be used in the practice of the invention is a phosphite having the formula $P(OR)_3$ wherein the three Rs are the same or different and each independently represents a substituted aryl group. The substituents may be of any kind provided that they do not interfere with the hydroformylation reaction. Examples of such phosphite are tris(2-methylphenyl) phosphite, tris(2,6-dimethylphenyl) phosphite, tris(2-isopropylphenyl) phosphite, tris(2-phenylphenyl) phosphite, tris(2-t-butylphenyl) phosphite, tris(2,4-di-t-butylphenyl) phosphite, tris(2-methyl-4-chlorophenyl) phosphite, bis (2-methylphenyl)(2-t-butylphenyl) phosphite, bis (2-t-butylphenyl)(2-methylphenyl) phosphite, and mixtures of these. Among them, tris(2-methylphenyl) phosphite, tris(2-t-butylphenyl) phosphite, tris(2,4-di-t-butylphenyl) phosphite, and mixtures of these are particularly suitable phosphites in carrying out the process according to the invention commercially since the use thereof in the hydroformylation of IPEA results in high rate of reaction and high selectivity toward MHP and since they are relatively readily available.

Several typical phosphorus ligands and their $\nu$ and $\theta$ values are shown below in Table A.

TABLE A

| Phosphorus ligand | $\nu$-value (cm$^{-1}$) | $\theta$-value (deg) |
|---|---|---|
| $P(C_6H_5)_3$ | 2068.9 | 145 |
| $P(C_6H_{13})_3$ | 2056.4 | 170 |
| $P(2\text{-}CH_3C_6H_4)_3$ | 2066.6 | 194 |
| $P(OC_6H_5)_3$ | 2085.3 | 128 |
| $P(O\text{—}2\text{-}CH_3C_6H_4)_3$ | 2084.1 | 141 |
| $P(O\text{—}2\text{-}isoC_3H_7C_6H_4)_3$ | 2084.6 | 148 |
| $P(O\text{—}2\text{-}C_6H_5C_6H_4)_3$ | 2085.0 | 152 |
| $P(O\text{—}2\text{-}t\text{-}C_4H_9C_6H_4)_3$ | 2086.1 | 175 |
| $P(O\text{—}2,6\text{-}CH_3.CH_3.C_6H_3)_3$ | 2083.2 | 190 |
| $P(O\text{-}iso\text{-}C_3H_7)_3$ | 2075.9 | 130 |
| $P(O\text{—}C_2H_5)_3$ | 2076.3 | 109 |

TABLE A-continued

| Phosphorus ligand | $\nu$-value (cm$^{-1}$) | $\theta$-value (deg) |
|---|---|---|
| $P(O\text{—}2,4\text{-}di\text{-}t\text{-}C_4H_9C_6H_3)_3$ | 2085.6 | 175 |

From Table A, it is apparent that tris(2-methylphenyl) phosphite, tris(2,6-dimethylphenyl) phosphite, tris(2,4-di-t-butylphenyl) phosphite and the like are phosphites to be preferred in the practice of the invention. It is surprising, however, that such phosphites, in particular tris(2,6-dimethylphenyl) phosphite, are inactive in the hydroformylation of branched olefins having no functional groups, such as 2-methyl-1-hexene.

The rhodium compound to be used in the practice of the present invention is a rhodium compound capable of catalyzing the hydroformylation or capable of being converted in the hydroformylation reaction system to a form capable of catalyzing the hydroformylation and includes, to be concrete, rhodium oxide; rhodium chloride; rhodium salts of organic carboxylic acids such as rhodium acetate and rhodium propionate; rhodium-carbonyl compounds such as $Rh_4(CO)_{12}$, $Rh_6(CO)_{16}$ and $[Rh(CO)_2Cl]_2$; di-$\mu$-chlorobis(1,3-cyclopentadiene)dirhodium; di-$\mu$-chlorobis(1,5-cyclooctadiene)dirhodium; rhodium acetylacetonate; and rhodium dicarbonyl acetylacetonate. Metallic rhodium carried on active carbon or the like may also be used. Among these, those rhodium compounds which occur in a high valence state can be used after treatment either within or outside the reaction system with an appropriate reducing agent such as carbon monoxide, hydrogen, sodium borohydride or formaldehyde. In the process according to the invention, the rhodium compounds show very high catalytic activity and therefore can be used in the reaction mixture in concentrations as low as 0.01–0.1 milligram atom (as rhodium) per liter. Lower concentration than 0.01 milligram atom of rhodium per liter are unsatisfactory in the rate of reaction from the industrial viewpoint, whereas higher concentration than 0.1 milligram atom of rhodium per liter render the rate of reaction excessively high, so that the reaction becomes hardly controllable and the catalyst cost uneconomically high.

The amount of the tris(substituted aryl) phosphite is of importance especially in increasing the rate of reaction and the selectivity toward MHP. In accordance with the invention, it is necessary to use the phosphite in an amount of 110–500 moles, preferably 150–300 moles, per gram atom of rhodium in the rhodium compound. When the phosphite amount is smaller than 110 moles per gram atom of rhodium, the rate of reaction and the selectivity toward MHP decrease and at the same time the heat stability of the catalyst decreases. Larger amounts than 500 moles rather tend to decrease the rate of reaction and are uneconomical.

In accordance with the invention, the hydroformylation reaction is carried out at a temperature within the range of 60°–150° C., preferably 90°–130° C. At temperatures lower than 60° C., the rate of reaction is low whereas, at temperatures exceeding 150° C., the stability of the rhodium compound present as the catalyst tends to be hardly maintained. The reaction pressure depends on the reaction temperature employed but, practically, a reaction pressure within the range of about 30–150 atmospheres, preferably 60–120 atmospheres, is generally used. Reaction pressures below 30 atmospheres are unfavorable since the selectivity of the reaction decreases. Although the reaction can of course be carried out even at a reaction pressure higher than 150 atmospheres, it is industrially advantageous from the apparatus and procedure viewpoints to maintain the pressure at 150 atmospheres or below.

The ratio between the raw material gases, namely hydrogen gas and carbon monoxide gas, when expressed in terms of the mole ratio of hydrogen/carbon monoxide in the feed gas at the entrance into the reactor, is preferably within the range of about 3/1 to ⅓. The simultaneous presence in the reaction system of a gas or gases inert to the hydroformylation reaction in small amounts is allowable. Such inert gases are, for example, methane, ethane, propane, nitrogen, helium, argon, carbon dioxide and dimethyl ether. Although the hydroformylation reaction is desirably carried out in the absence of a solvent, it is also possible to carry out the reaction in the presence of a solvent which is inert within the reaction system. Examples of the solvent are alcohols such as ethanol, butanol, 3-methylbutanol and 3-methylpentane-1,5-diol; saturated aliphatic hydrocarbons such as pentane, hexane, heptane, octane, nonane and decane; aromatic hydrocarbons such as benzene, toluene, xylene and alkylnaphthalene; and ethers such as tetrahydrofuran.

In the practice of the invention, it is preferable to add a tertiary organic amine in amounts within the range of 1 mole to 100 moles per gram atom of rhodium to thereby prevent the acetal formation from MHP which tends to take place due to trace amounts of acids occurring in the raw materials or formed during the reaction. Examples of the tertiary organic amine which are suited for this purpose are tertiary aliphatic alkylamines such as triethylamine, tributylamine, tri-n-octylamine and N,N-dimethyl-2-ethylhexylamine; alkyl-substituted tertiary diamines such as N,N,N',N'-tetramethyl-1,2-diaminoethane, N,N,N',N'-tetramethyl-1,3-diaminopropane and N,N,N',N'-tetramethyl-1,4-diaminobutane; tertiary alkanolamines such as N,N-diethylethanolamine and triethanolamine; alicyclic tertiary amines such as N-methylpiperidine, N-methylpyrrolidine and N-methylmorpholine; and cyclic unsaturated tertiary amines such as pyridine, picoline and lutidine.

In the practice of the invention, the hydroformylation reaction may either be driven to such an extent that the conversion of IPEA reaches 100% or be controlled so that the conversion may not reach 100%. When the conversion of IPEA is kept below 100%, it is possible to obtain prenol, which is formed by isomerization of IPEA, in larger amounts than isovaleral, a product of further isomerization of prenol.

The reaction mixture obtained after the hydroformylation reaction can be distilled at a temperture of about 130° C. or below to thereby isolate the primary product MHP and so forth. The rhodium catalyst contained in the distillation residue after distillation at 130° C. or below may either be taken out of the reaction system for recovery thereof or wholly or partly be recycled to the hydroformylation reaction apparatus for reuse thereof. In either case, the process according to the invention is advantageous from the industrial viewpoint since the rhodium concentration is very low in said process.

The following examples are further illustrative of the invention but are by no means limitative of the invention.

EXAMPLE 1

A 300-ml stainless steel autoclave equipped with a magnetic stirrer was charged, in a hydrogen-carbon monoxide mixed gas (oxo gas; mole ratio: 1:1) atmosphere, with 98 ml of IPEA and 2 ml of a solution of 23.37 mg (0.0312 millimole) of $Ph_4(CO)_{12}$ and 11.95 g (25 millimoles) of tris(2-t-butylphenyl) phosphite in 100 ml of IPEA. (The amount of IPEA charged was 0.94 mole, the rhodium concentration in the IPEA charged was, on the rhodium atom basis, 0.025 milligram atom per liter and the phosphite concentration was 5 millimoles per liter.)

Then, while maintaining the autoclave inside pressure at 90 atmospheres with the same oxo gas as mentioned above, the reaction mixture was heated with stirring to thereby raise the inside temperature to 120° C. over 30 minutes. The inside temperature was maintained at 120° C. and the reaction was carried out for 3 hours. During the reaction, the same hydrogen-carbon monoxide mixed gas as mentioned above (mole ratio: 1:1) was supplied continuously through a pressure-adjusting valve to thereby maintain the autoclave inside pressure always at 90 atmospheres, while the rate of flow of the effluent gas from the autoclave was adjusted to about 5 liters per hour. When the reaction period was over, the reaction mixture was sampled via a sampling port. Analysis of the sample by gas chromatography showed that 10% of the IPEA remained unreacted and that the yields of isovaleral, prenol and MHP were 8.5%, 8.6% and 82.0%, respectively, on the converted IPEA basis.

EXAMPLE 2 AND COMPARATIVE EXAMPLES 1-3

Using a 100-ml stainless steel autoclave equipped with a magnetic stirrer, IPEA and 2-methyl-1-hexene were respectively hydroformylated in a hydrogen-carbon monoxide mixed gas (mole ratio: 1:1) atmosphere in the presence of $Rh(CO)_2$(acetylacetonate) and tris(2-t-butylphenyl) phosphite under the conditions specified below in Table 1. In Table 1, the P/Rh ratio is the atom ratio between the phosphorus compound and the rhodium compound.

TABLE 1

| Example & Comparative Example | Olefin | Rh concn. (mmole/l) | P/RH ratio | Reaction temp. (°C.) | Reaction period (hrs) | Reaction pressure (kg/cm²) |
|---|---|---|---|---|---|---|
| Example 2 | IPEA | 0.05 | 250 | 100 | 2.5 | 50 |
| Comparative Example 1 | IPEA | 0.05 | 10 | 100 | 2.5 | 20 |
| Comparative Example 2 | 2-methyl-1-hexene | 1.0 | 10 | 80 | 1.0 | 14 |
| Comparative Example 3 | 2-methyl-1-hexene | 1.0 | 120 | 80 | 1.0 | 14 |

The results of each reaction run are shown below in Table 2. The olefin conversion and the selectivity were calculated as follows:

Olefin conversion (mole percent)=(amount of olefin consumed/amount of olefin charged)×100

Selectivity (mole percent)=(amount of desired product formed/amount of all products formed)×100

The selectivity values shown in Table 2 for Example 1 and Comparative Example 1 are selectivities toward MHP and those shown for Comparative Examples 2 and 3 are selectivities toward 3-methylheptanal.

TABLE 2

| Example & Comparative Example | Conversion of starting olefin (mole percent) | Selectivity (mole percent) |
|---|---|---|
| Example 2 | 72 | 83 |
| Comparative Example 1 | 48 | 28 |
| Comparative Example 2 | 93 | 95 |
| Comparative Example 3 | 0 | 0 |

The above results indicate that when IPEA is hydroformylated using the phosphite in an amount of about 10 moles per gram atom of rhodium in accordance with the disclosure in Japanese Patent Application Laid Open No. 123134/1982, the rate of reaction and the selectivity are both very low and that when 2-methyl-1-hexene, which is a branched olefin having no functional group, is formylated using the phosphite in an amount of 120 moles per gram atom of rhodium after the mode of practice of the present invention, the hydroformylation reaction does not occur at all. Furthermore, the amount of the rhodium catalyst used in Comparative Examples 2 and 3 is relatively too large. In view of the above, it is evident that the process according to the present invention is an industrially advantageous process.

EXAMPLE 3 AND COMPARATIVE EXAMPLES 4–5

The same reaction apparatus as used in Example 1 was charged with IPEA (0.94 mole), $Rh_4(CO)_{12}$ (0.025 milligram atom per liter as calculated on the rhodium atom basis) and tris(2-t-butylphenyl) phosphite (in an amount corresponding to the P/Rh ratio specified in Table 3) and the reaction was carried out in the same manner as in Example 1 at a pressure of 60 atmospheres and a temperature of 120° C. (Example 3). The results thus obtained are shown in Table 3. The P/Rh ratio is the atom ratio between the phosphorus compound and the rhodium compound.

The reaction was also carried out at a P/Rh ratio of 100 (Comparative Example 4) or 600 (Comparative Example 5). The results thus obtained are shown in Table 3. The effects of the invention are apparent from these results.

TABLE 3

| Example & Comparative Example | P/Rh ratio | Conversion of IPEA (mole percent) | Selectivity toward MHP (mole percent) |
|---|---|---|---|
| Example 3 | 150 | 78 | 77 |
| Comparative Example 4 | 100 | 48 | 61 |
| Comparative Example 5 | 600 | 55 | 79 |

EXAMPLE 4

IPEA was hydroformylated in the same manner and under the same conditions as in Example 1 except that tris(2,4-di-t-butylphenyl) phosphite was used in place of tris(2-t-butylphenyl) phosphite in the same molar concentration. Analysis of the thus-obtained reaction mixture by gas chromatography showed that 10% of the IPEA remained unreacted and that the yields of isovaleral, prenol and MHP were 8.2%, 8.8% and 82.0%, respectively on the converted IPEA basis.

EXAMPLE 5

IPEA was hydroformylated in the same manner and under the same conditions as in Example 1 except that the reaction pressure was maintained at 40 atmospheres. After the reaction, 24% of the IPEA remained unreacted, and the yields of isovaleral, prenol and MHP were 8.0%, 12.5% and 76.0%, respectively on the converted IPEA basis.

EXAMPLE 6

IPEA was hydroformylated in the same manner and under the same conditions as in Example 1 except that tris(2-methylphenyl) phosphite was used in lieu of tris(2-t-butylphenyl) phosphite in the same molar concentration and that triethanolamine was further added to the reaction system in an amount of 30 mg (corresponding to a concentration of 2 millimoles per liter of whole liquid charge). Analysis of the thus-obtained reaction mixture by gas chromatography showed that 18% of the IPEA remained unreacted and that the yields of isovaleral, prenol and MHP were 3.2%, 7.3% and 87.2%, respectively on the converted IPEA basis.

EXAMPLE 7

IPEA was hydroformylated in the same manner and under the same conditions as in Example 1 except that tris(2-isopropylphenyl) phosphite was used in lieu of tris(2-t-butylphenyl) phosphite in the same molar concentration and that the reaction temperature was 110° C. and the reaction period 4 hours. Analysis of the thus-obtained reaction mixture by gas chromatography showed that 14% of the IPEA remained unreacted and that the yields of isovaleral, prenol and MHP were 4.8%, 7.8% and 86.0%, respectively on the converted IPEA basis.

COMPARATIVE EXAMPLE 6

IPEA was subjected to hydroformylation in the same manner as in Example 7 except that triphenylphosphine was used in lieu of tris(2-isopropylphenyl) phosphite in the same molar concentration. Analysis of the thus-obtained reaction mixture by gas chromatography showed that 86% of the IPEA remained unreacted, indicating scarce progress of the reaction.

COMPARATIVE EXAMPLE 7

IPEA was subjected to hydroformylation in the same manner as in Example 7 except that tris(2-methylphenyl) phosphine was used in lieu of tris(2-isopropylphenyl) phosphite in the same molar concentration. Analysis of the thus-obtained reaction mixture by gas chromatography indicated that 71% of the IPEA remained unreacted and that the yields of isovaleral, prenol and MHP were 6.3%, 20.0% and 71.4%, respectively on the converted IPEA basis.

COMPARATIVE EXAMPLE 8

IPEA was subjected to hydroformylation in the same manner as in Example 7 except that triphenyl phosphite was used in lieu of tris(2-isopropylphenyl) phosphite in the same molar concentration. Analysis of the thus-obtained reaction mixture showed that 66% of the IPEA remained unreacted and that the yields of isovaleral, prenol and MHP were 1.0%, 9.1% and 86.0%, respectively on the converted IPEA basis.

EXAMPLE 8

The same reaction apparatus as used in Example 1 was charged, in an atmosphere of a hydrogen-carbon monoxide mixed gas (mole ratio: 1:1), with 98 ml of IPEA and 2 ml of a solution prepared by dissolving 27.58 mg (0.0624 millimole) of $Rh_2(OCOCH3)_4$ and 9.85 g (25 millimoles) of tris(2,6-dimethylphenyl) phosphite in 100 ml of IPEA and then adding thereto 3.8 mg (0.1 millimole) of sodium borohydride with stirring. (The IPEA charged amounted to 0.94 mole, the concentration of the rhodium compound in the IPEA charged as calculated on the rhodium atom basis was 0.025 milligram atom per liter and that of the phosphite was 5 millimoles per liter.)

Then, the hydroformylation reaction was allowed to proceed in the same manner as in Example 1 at 120° C. for 3 hours while the pressure within the autoclave was maintained at 120 atmospheres with the same oxo gas as mentioned above. Analysis of the thus-obtained reaction mixture revealed that 22% of the IPEA remained unreacted and that the yields of isovaleral, prenol and MHP were 8.2%, 16.0% and 74.3%, respectively on the converted IPEA basis.

EXAMPLE 9

The procedure of Example 1 was exactly followed (first run). The reaction mixture obtained was transferred via the sampling port to a distillation apparatus with care not to allow contact with air. The reaction mixture in the distillation apparatus was distilled at a distillate temperature of about 70° C. until about 97% of said mixture was distilled off. IPEA (98 ml) was added to the distillation residue, the resultant mixture was charged again into the autoclave in an oxo gas atmosphere, and the reaction was carried out in the same manner as in the first run. In this way the reaction was repeated four times in total. It was found that the catalyst can be recycled for repeated successful use. The results obtained in the repeated runs are shown in Table 4.

TABLE 4

| Repeated run No. | Conversion of IPEA (%) | Selectivity (%) on the converted IPEA basis toward | | |
|---|---|---|---|---|
| | | Isovaleral | Prenol | MHP |
| 1 | 90 | 8.5 | 8.6 | 82.0 |
| 2 | 91 | 8.2 | 8.5 | 82.3 |
| 3 | 89 | 8.0 | 8.5 | 82.6 |
| 4 | 88 | 8.5 | 8.3 | 82.0 |

EXAMPLE 10

IPEA was hydroformylated in the same manner and under the same conditions as in Example 7 except that the rhodium concentration in the IPEA charged as calculated on the rhodium atom basis was 0.0125 milligram atom per liter and that the reaction temperature was 135° C. Analysis of the thus-obtained reaction mixture by gas chromatography showed that 7% of the IPEA remained unreacted and that the yields of isovaleral, prenol and MHP were 11.3%, 7.0% and 80.2%, respectively on the converted IPEA basis.

EXAMPLE 11

The same reaction apparatus as used in Example 1 was charged with IPEA (100 ml, 0.94 mole), $Rh_4(CO)_{12}$ in an amount, on the rhodium atom basis, of 0.0625 milligram atom per liter, and tris(2-t-butylphenyl) phosphite in an amount of 30 millimoles per liter, and the reaction was carried out in the same manner as in Example 1 except that the reaction temperature was 80° C. and the reaction period 5 hours and that the inside pressure was maintained at 90 atmospheres with a 1:1 (mole ratio) hydrogen-carbon monoxide mixed gas. After the reaction period was over, the reaction mixture was analyzed by gas chromatography. It was revealed that 22% of the IPEA remained unreacted and that the yields of isovaleral, prenol and MHP were 2.9%, 9.4% and 87.0%, respectively on the converted IPEA basis.

What is claimed is:

1. A process for producing 2-hydroxy-4-methyltetrahydropyran by reacting 3-methyl-3-buten-1-ol with a hydrogen-carbon monoxide mixed gas in the presence of a rhodium compound, characterized in that the rhodium compound is used in a concentration of 0.01–0.1 milligram atom (on the rhodium atom basis) per liter and that the reaction is carried out in the simultaneous presence of a tris(alkyl substituted phenyl) phosphite of the formula $P(OR)_3$ wherein three Rs are the same or different and each is an alkyl substituted phenyl, in an amount of 110–500 moles per gram atom of rhodium, said tris(alkyl substituted phenyl) phosphite having an electronic parameter ($v$-value) of 2080–2090 $cm^{-1}$ and a steric parameter ($\theta$-value) of 135°–190°.

2. The process of claim 1, wherein said tris(alkyl substituted phenyl) phosphite is used in an amount of 150–300 moles per gram atom of rhodium.

3. The process of claim 1, wherein said tris(alkyl substituted phenyl) phosphite is tris(2-methylphenyl)-phosphite, tris(2-t-butylphenyl) phosphite, tris(2,4-di-t-butylphenyl) phosphite, or a mixture of these.

4. The process of claim 1, wherein the reaction is carried out at a pressure of 30–150 atmospheres.

5. The process of claim 1, wherein the reaction is carried out at a pressure of 60–120 atmospheres.

6. The process of claim 1, wherein the reaction is carried out at a temperature of 60°–150° C.

7. The process of claim 1, wherein an organic tertiary amine is further added to the reaction system in an amount of 1–100 moles per gram atom of rhodium.

* * * * *